United States Patent [19]

Lieb et al.

[11] Patent Number: 4,477,252

[45] Date of Patent: Oct. 16, 1984

[54] FIBER OPTIC SYSTEM FOR DENTAL HANDPIECE

[75] Inventors: Nathaniel H. Lieb, Narberth; Albert D. Alderman, Jr., Skippack; James L. Alago, Lansdale, all of Pa.

[73] Assignee: Venture Technology, Inc., West Conshohocken, Pa.

[21] Appl. No.: 413,021

[22] Filed: Aug. 30, 1982

[51] Int. Cl.³ .............................. A61C 1/05; A61C 3/00
[52] U.S. Cl. ........................................ 433/29; 433/126
[58] Field of Search ............................ 433/29, 99, 126

[56] References Cited

U.S. PATENT DOCUMENTS

| | | | |
|---|---|---|---|
| 3,634,938 | 1/1972 | Hutchinson | 433/29 |
| 3,955,284 | 5/1976 | Balson | 433/126 X |
| 4,020,556 | 5/1977 | Sotman . | |
| 4,171,572 | 10/1979 | Nash . | |
| 4,313,725 | 2/1982 | Lieb et al. | 433/126 |
| 4,330,274 | 5/1982 | Friedman et al. | 433/29 |
| 4,334,863 | 6/1982 | Magid et al. | 433/29 |
| 4,341,518 | 7/1982 | Wallace | 433/29 |
| 4,403,957 | 9/1983 | Mössle et al. | 433/29 |

OTHER PUBLICATIONS

Brochure entitled Midwestern American Fiber Optic System-Copyright 1979.

*Primary Examiner*—Robert P. Swiatek
*Attorney, Agent, or Firm*—Caesar, Rivise, Bernstein & Cohen, Ltd.

[57] ABSTRACT

A dental handpiece having a mechanism for mounting a bur in one end thereof. A fiber optic system is mounted within the handpiece, and is adapted to direct light adjacent the bur when it is rotating to aid a dentist in using the handpiece. The fiber optic system includes a bulb mounted within the handpiece, which bulb is secured in a housing formed from a heat-resistant plastic. Air used for driving the handpiece is also used to cool the heat generated by the light. A pneumatic switch is provided for automatically turning on the light when the handpiece is used and for automatically turning off the light when use of the handpiece is terminated.

16 Claims, 14 Drawing Figures

FIBER OPTIC SYSTEM FOR DENTAL HANDPIECE

This invention relates to a dental handpiece, and more particularly, to a dental handpiece including a novel fiber optic system.

Illumination of the work area within the mouth has received a great deal of attention due to the importance of the problem, and a wide variety of devices have been employed by dentists for this purpose. The devices include a reflector on the forehead of the dentist, overhead lights, and more recently, fiber optic bundles or light conductors within the dental handpiece. The fiber optic systems terminate adjacent the bur secured in the handpiece, and directly illuminated the area being treated by the dentist.

A number of systems have been developed which incorporate fiber optic bundles within the handpiece, and the source of light is provided by a remote lamp in its own housing, which lamp is cooled by a fan. The light is transmitted to the handpiece through fiber optic bundles connected with the light and the handpiece. Systems of this type are shown in U.S. Pat. Nos. 4,020,556 and 4,171,572.

The use of fiber optic systems with remote lights has presented a number of problems. The tubes containing the fiber optic bundles which connect the handpiece to the remote light are relatively heavy, and add to the weight of the handpiece, thereby making the use of the handpiece more fatiguing to the dentist. Also, the fiber bundle in the tube can break, thereby reducing the light intensity. Additionally, the fiber bundle within the tube limits the flexibility of use of the dental handpiece, and this makes the handpiece more difficult to use by the dentist.

An improvement in the fiber optic lighting systems for dental handpieces has been the use of a small quartz-halogen bulb mounted within the handpiece, which bulb directs the light directly into a fiber optic bundle within the handpiece. Having the bulb within the handpiece obviates the problems of having a light source remote from the handpiece, and the necessity of having a long tube containing a fiber optic bundle connecting the remote light with the handpiece. The use of bulbs within the handpiece is shown in U.S. Pat. Nos. 4,330,274 and 4,334,863.

One of the problems of having a bulb within the handpiece is that of cooling the bulb. Thus, the bulb will become quite hot during use, and unless it is adequately cooled, it will quickly burn out, and in addition, it will heat the handle of the handpiece, thereby making it difficult for the dentist to continue to hold the handpiece. The problem of heating by the bulb is recognized in U.S. Pat. No. 4,334,863, and a means of solving the problem is set forth in the patent. In one aspect of this invention, a novel mechanism for cooling the bulb is provided. The operation of the cooling mechanism in this invention is distinctly different from that disclosed in U.S. Pat. No. 4,334,863.

In another aspect of this invention, a unique switch is provided for automatically turning the light on when air is admitted to the handpiece for driving the turbine. The means for cooling the bulb in the handpiece is the exhaust air emanating from the turbine housing after the turbine has been driven. Whenever air is admitted to drive the handpiece, the light will be turned on, and the air will cool the light bulb. When the dentist ceases using the handpiece, and the supply of air to the handpiece is stopped, the light will automatically be turned off. This insures that whenever the handpiece is being used, there will be a source of air to cool the light. Alternatively, when the handpiece is not being used, the light will automatically be turned off, and there is no problem of burning out the bulb when the handpiece is not being used.

The mechanism for turning the light on or off is a pneumatic switch, which is closed when air is admitted to the handpiece. In U.S. Pat. No. 4,334,863, a pneumatic switch is broadly disclosed for operating the handpiece in a manner similar to the operation of the handpiece of this invention. However, no details of the pneumatic switch are disclosed in the patent.

The device disclosed in U.S. Pat. No. 4,334,863 is being sold by the Midwest American Dental Division of American Hospital Supply Corp. As part of the system being sold, there is a pneumatic switch that is actuated by the dentist's foot control which furnishes air to the handpiece. The switch includes a metal diaphragm which completes a circuit when air under pressure bears against one side of the diaphragm. The entire switch is embodied in a sealed unit, and if the unit should malfunction, the entire unit must be replaced.

In the device of this invention, control of the pneumatic switch is through a rubber diaphragm. The switch is easily disassembled and reassembled, and any part thereof is easily replaceable.

It is accordingly an object of this invention to provide a novel fiber optic system for a dental handpiece.

It is another object of this invention to provide a dental handpiece having an internal fiber optic system and an internal light source therefor.

It is a further object of this invention to provide a dental handpiece with an internal fiber optic system and bulb therefor, with a novel means for cooling the bulb.

It is yet a further object of this invention to provide a dental handpiece with a novel internal fiber optic light system in combination with a pneumatic switch.

These and other objects of the invention are accomplished by providing a dental handpiece comprising a hollow handle, a turbine mounted at one end thereof, means for securing a dental bur within said turbine, means for supplying air to rotate said turbine, a fiber optic lighting system mounted within said handle, said system including a bulb housing formed from a heat-resistant plastic, a bulb mounted within said housing, light transmitting fibers within said housing, said fibers having one end terminating adjacent said bulb and the other end terminating at said end of said handle, whereby light emanating from said bulb passes through said fibers and onto the area adjacent said bur, a channel passing through said housing, and means for directing exhaust air from said turbine through said channel, whereby said exhaust air aids in cooling said bulb.

Other objects and many of the intended advantages of this invention will be readily appreciated as the same becomes better understood by reference to the following detailed description when considered in connection with the accompanying drawings wherein:

Figure 1:
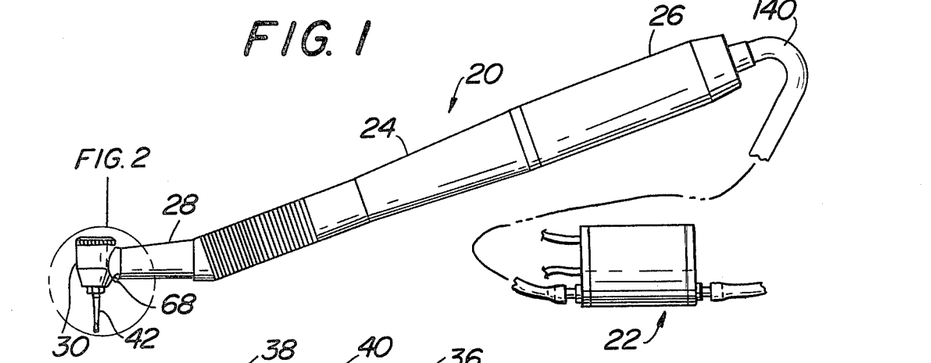
FIG. 1 is a side elevational view of the handpiece of this invention, including the pneumatic switch.

Referring now in greater detail to the various figures of the drawings wherein like reference characters refer to like parts, an air driven dental handpiece including the fiber optic system of this invention is generally shown at 20 in FIG. 1. The pneumatic switch forming a part of the invention is shown at 22 in FIG. 1.

As seen in FIG. 1, handpiece 20 includes a hollow handle 24, a coupling 26 secured on one end thereof, an angled neck 28 and a turbine housing 30 mounted on the neck. A rotor or turbine 32 (FIG. 2) is mounted in turbine housing 30. The hollow shaft 33 of rotor 32 is mounted in upper and lower ball bearings 34. An end cap 36 threadedly secures the rotor and its associated bearings in place. A wavy spring 38 bears against the outer race of upper ball bearing 34, thereby loading the bearings. An opening 40 is formed in end cap 36 for insertion of a tool used in securing and removing a dental bur 42 from shaft 33.

Figure 2:
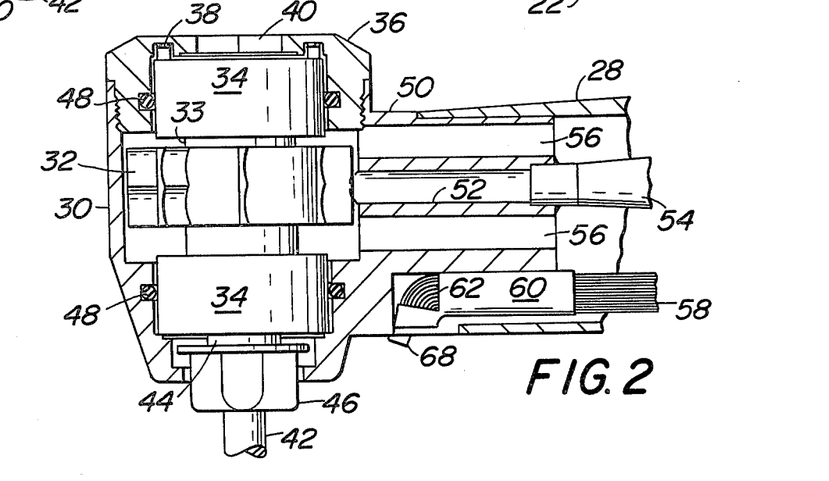
FIG. 2 is an enlarged sectional view taken in the area designated as FIG. 2 in FIG. 1.

A collet 44 is threadedly secured in rotor shaft 33. A nut 46 is threadedly secured on the collet 44, and is used for tightening the collet. The ball bearings 34 are mounted in rubber O-rings 48.

To the extent described, the head of the handpiece of this invention is basically the same as that shown in U.S. Pat. No. 4,313,725, owned by the assignee of this application. The method of securing the bur 42 in the handpiece is disclosed in further detail in U.S. Pat. No. 4,313,725, the disclosure of which is incorporated by reference herein. Although this invention is described with respect to the handpiece shown in U.S. Pat. 4,313,725, it should be understood that the invention is adapted for use with any air driven dental handpiece known to the art.

Turbine housing 30 includes an extension 50, which is secured in neck 28 by a pressed fit. A channel 52 is formed in extension 50, and a conduit 54 is in fluid communication with channel 52. Air under pressure enters conduit 54, passes through channel 52 and drives the turbine 32. The exhaust air from the turbine 32 passes through channel 56, which is concentric with channel 52.

Figure 3:
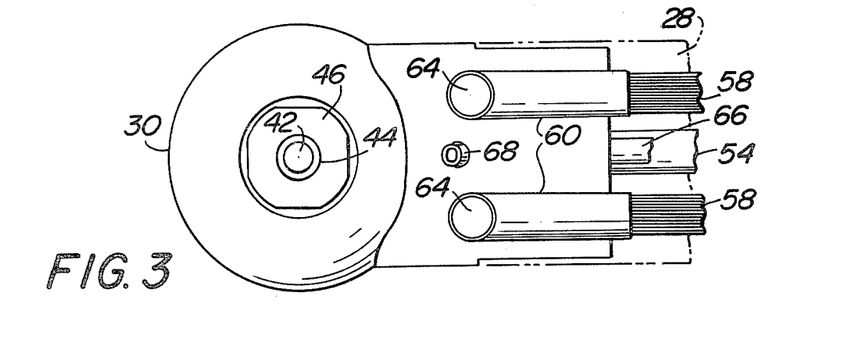
FIG. 3 is a bottom plan view of the front of the handpiece shown in FIG. 2.

As seen in FIG. 3, a pair light transmitting, fiber optic bundles 58 pass through neck 28 and are mounted in extension 50 by sleeves 60. As seen in FIG. 2, each sleeve 60 includes a cut-out notch 62 to permit the bending of the fiber optic bundles 58. As seen in FIG. 3, each fiber optic bundle has a terminus 64. Light passing through the fiber optic bundles emanates from the termini 64, and is directed to the area of the rotating bur 42.

A conduit 66 passes through neck 28 and through extension 50, and has a downwardly projecting end 68. A coolant water spray emanates from end 68, and is directed against the rotating bur 42, in a manner well known to the art.

Figures 4, 5, 6:
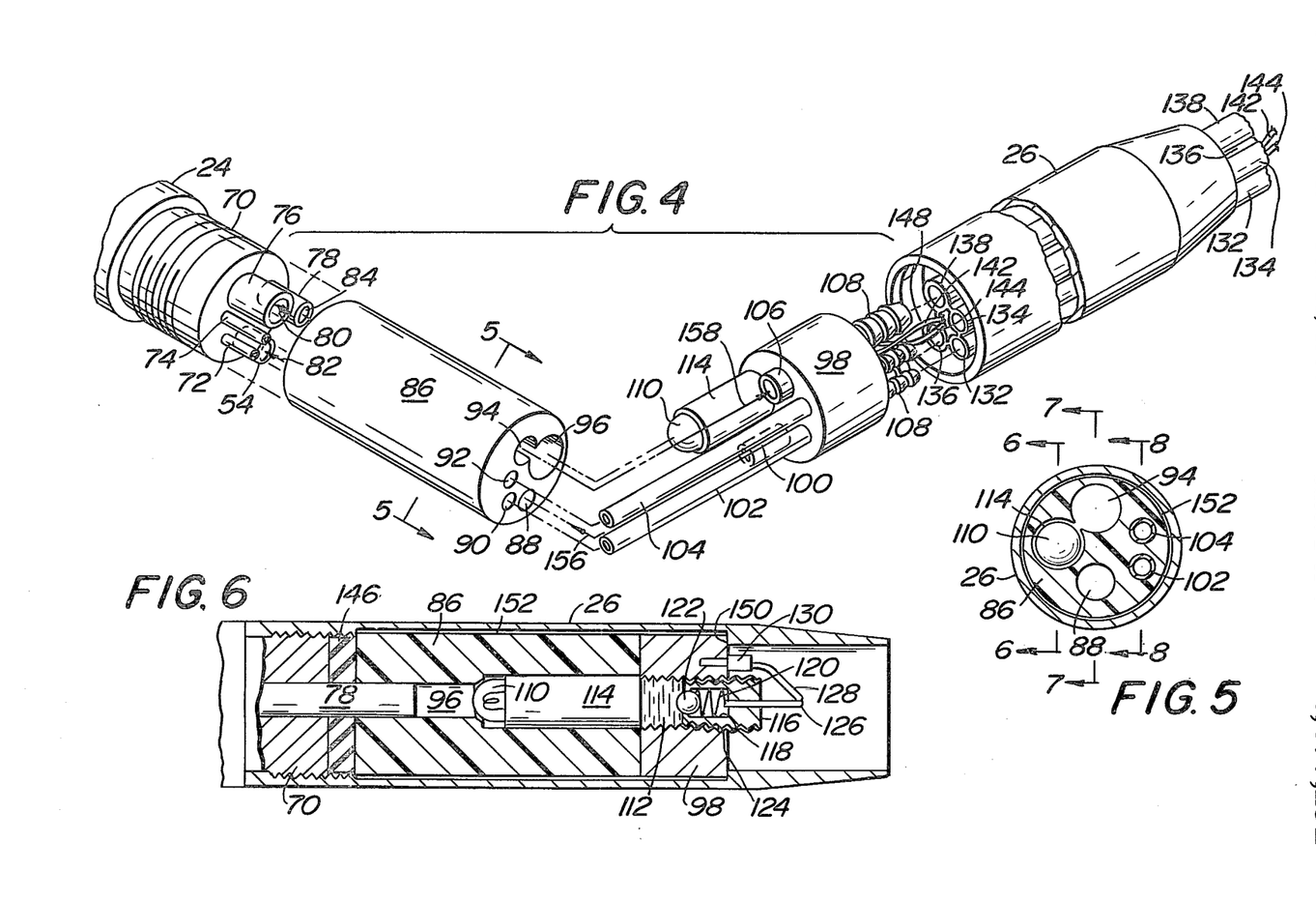
FIG. 4 is an exploded perspective view of the internal fiber optic system of the handpiece.
FIG. 5 is a sectional view taken along the line 5—5 of FIG. 4.
FIG. 6 is an enlarged sectional view taken along the line 6—6 of FIG. 5.

Referring now to FIG. 4, the fiber optic system and associated lamp are shown in exploded perspective therein. As seen in FIG. 4, the rear of the hollow handle 24 is shown and the coupling 26 is shown as being broken away, for the purpose of clarity. A cylindrical plug 70 is secured in the rear of handle 24 by a pressed fit. The exterior of plug 70 is threaded. Tubes or conduits 54, 72, 74, 76 and 78 pass through plug 70, and into the interior of handle 24. Tube 54 supplies the air for driving the turbine (FIG. 2). Tube 72 supplies water and tube 74 supplies air, with the air and water conduits combining to form an air-water mist that emanates from end 68 (FIG. 2) to form a coolant mist directed at the bur 42. The exhaust air passing through channel 56 (FIG. 2) leaves conduit 76 and plug 70, as indicated by arrow 80. Arrow 82 in FIG. 4 indicates the path of travel of the drive air for the turbine. Conduit 78 contains a fiber optic bundle 84. The bundle 84 is bifurcated in handle 24, and is used to form bundles 58 (FIG. 3). The use of bifurcated fiber optic bundles for light transmitting purposes in dental handpieces is known to the art, as shown in U.S. Pat. No. 4,020,556.

A cylindrical housing 86 is positioned behind plug 70. Housing 86 is formed from a heat-resistant plastic. A preferred plastic is polytetrafluoroethylene (Teflon). Other heat-resistant plastics known to the art can also be used in carrying out this invention. Another plastic that may be used is a polytetrafluoroethylene-polyimide plastic, such as that being sold under the Trademark Vespel by E. I. du Pont de Numours & Co. Parallel channels 88, 90, 92, 94 and 96 are formed in housing 86, and pass entirely therethrough. Channels 88, 90 and 92 are isolated from each other, and channels 94 and 96 are in fluid communication with each other throughout their lengths.

Figure 7:
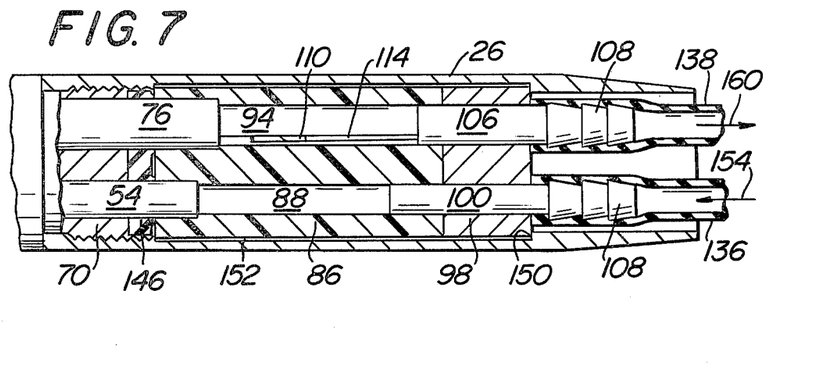
FIG. 7 is an enlarged sectional view taken along the line 7—7 of FIG. 5.
Figure 8:
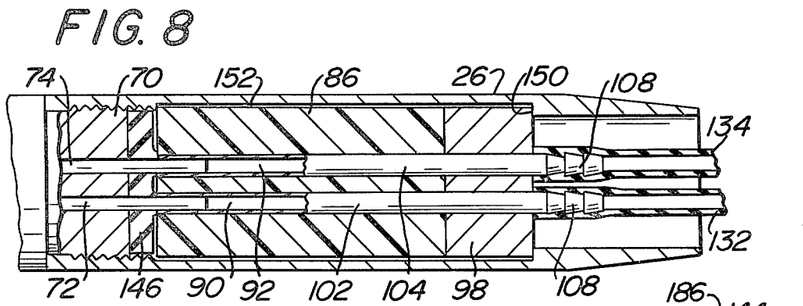
FIG. 8 is enlarged sectional view taken along the line 8—8 of FIG. 5.

A connector 98 is positioned behind housing 86. Conduits 100, 102, 104 and 106 pass through connector 98. Each of said conduits has a ferruled end 108 (FIGS. 7 and 8). A bulb 110 having a threaded end 112 (FIG. 6) is threadedly secured in connector 98. Bulb 110 is a quartz-halogen bulb, which is a standard type of bulb used in fiber optic systems for dental handpieces. A brass sleeve 114 is positioned around bulb 110. Connector 98 is electrically conductive, and is formed from a suitable metal, such as aluminum.

A stainless steel socket 116 (FIG. 6) is threadedly received in the rear of connector 98. As seen in FIG. 6, socket 116 includes an internal bore 118. Positioned within the bore 118 is a compression spring 120 and a ball contact 122. Socket 116 is electrically insulated from connector 98 by a plastic insulating sleeve 124, which can be formed from any suitable plastic, such as polytetrafluoroethylene (Teflon). A lead 126 is secured in socket 116, and is in electrical contact therewith. A second lead 128 is secured in connector 98 by pin contact 130.

Flexible tubes 132, 134, 136 and 138 enter the rear of handpiece 20 through coupling 26 (FIG. 4). The flexible tubes are all contained in an outer flexible tube 140

(FIG. 1) which is secured on the rear end of coupling 26 in a conventional manner. Electrical lines 142 and 144 also enter the handpiece through coupling 26. Lines 142 and 144 are connected to leads 126 and 128 in any conventional manner, as by soldering. As explained hereinafter, lines 142 and 144 are used for completing a circuit through bulb 110, thereby illuminating the bulb.

The assembly of the handpiece will now be described, by reference to FIGS. 5, 6, 7 and 8. A rubber gasket 146 is positioned against plug 70, and tubes 54, 72, 74, 76 and 78 pass therethrough. Housing 86 is then telescoped over the tubes, and is positioned agains gasket 146. Referring to FIG. 6, it is seen that tube 78 containing the fiber optic bundle 84 is received in channel 96 of housing 86. Also positioned in channel 96, and entering from the rear end thereof, is bulb 110 and its associated sleeve 114. Lines 142 and 144 are connected to leads 126 and 128 (not shown in FIG. 6, for the purpose of clarity).

After the lines 142 and 144 have been connected, and after the other connections within housing 86, to be described hereinafter, have been made, the coupling 26 is secured in place. The internal diameter of coupling 26 is larger than the external diameter of housing 86 and connector 98, and is adapted to be slid thereover after the connections have been made. As seen in FIG. 4, the front end of coupling 26 is internally threaded, as shown at 148. After the necessary connections have been made in housing 86 and with connector 98, the sleeve is slid over the housing and connector, and threadedly secured on plug 70, as seen in FIGS. 6, 7 and 8. Coupling 26 includes an inner shoulder 150, which bears against the rear edge of connector 98. When the coupling is threadedly secured in place, it securely holds housing 86 and connector 98 in place by the pressure brought by shoulder 150 against connector 98 and the aligned housing 86. The gasket 146 is compressed when the coupling 26 is screwed in in place.

In the assembly of the handpiece, conduit 76 is positioned in channel 94 of housing 86 (FIG. 7). Conduit 106 enters the other end of channel 94. Flexible tube 138 is secured on ferruled end 108 of conduit 106, and tubes 138 passes through the rear of the handpiece (FIG. 4).

As further seen in FIG. 7, conduit 54 is positioned in channel 88 of housing 86. Conduit 100 is also positioned in channel 88 at the rear end thereof. Flexible tube 136 is secured on the ferruled end 108 of conduit 100, and tube 136 passes through the rear end of coupling 26.

As seen in FIG. 8, conduits 102 and 104, which project through connector 98, pass through channels 90 and 92, respectively, in housing 86, and terminate at the forward end thereof. Conduits 72 and 74 pass through gasket 146, and are received in conduits 102 and 104, respectively. Flexible tubes 132 and 134 are secured on ferruled ends of conduits 102 and 104, and pass through the rear of coupling 26.

The outer diameters of housing 86 and connector 98 are slightly smaller than the inner diameter of coupling 26, thereby leaving an annular space 152. The annular space impedes the transfer of heat from housing 86 and connector 98 to the coupling 26, which reduces the heat transfer from the bulb to the coupling. This, in turn, reduces the discomfort to the dentist when using the handpiece 20.

The operation of the handpiece 20 will now be described. In operating the handpiece, an automatic control is provided, which control will be described hereinafter. However, the handpiece can be operated through any known control means, and the function of the handpiece will be the same, regardless of the control means.

When the handpiece is actuated, light bulb 110 is illuminated by current furnished through lines 142 and 144. At the same time, air for driving the turbine 32 enters through flexible tube 136 (FIG. 7) as indicated by arrow 154. The air continues through channel 88 in housing 86 (see arrow 156 in FIG. 4), and into conduit 54 (arrow 82 in FIG. 4). The air then enters channel 52 (FIG. 2) and rotates the turbine 32, in a manner known to the art.

The drive air then leaves the turbine housing 30 through channel 56 (FIG. 2). It passes through conduit 76 (FIG. 4) as indicated by arrow 80. The exhaust air then passes through channel 96 in housing 86, through conduit 106 in connector 98 (FIG. 4) and out through flexible tube 138. The path of travel of the exhaust air is indicated by arrow 158 in FIG. 4 and arrow 160 in FIG. 7.

Referring to FIGS. 4, 5 and 7, it is seen that channel 94 is in fluid communication with channel 96, which latter channel houses bulb 110 and associated sleeve 114. Accordingly, as the exhaust air passes through the handpiece, it will contact the bulb and its associated sleeve. The air serves to cool the bulb and is associated sleeve, and accordingly keeps the heat generated by the bulb to a minimum.

It is thus seen that the device of this invention provides three separate means of preventing heat transfer from the bulb to the user of the handpiece. The first means is the coolant air which passes over the bulb and its associated sleeve. The second means of preventing heat transfer is the use of the heat-resistant plastic forming the housing 86. The third means of minimizing heat transfer is the provision of the annular air gap 152 between the housing 86 and the coupling 26. In addition to the foregoing, the exhaust air also serves to cool the bulb, thereby prolonging the life of the bulb. Without the coolant air, the bulb could rapidly overheat, and this would result in bulb failure.

Referring again to FIG. 8, when air is admitted to drive the handpiece, at the same time, air enters flexible tube 134 and water enters flexible tube 132. The air and water pass through their associated conduits and channels, and are ultimately mixed within handle 24, from which the mixture will emanate at end 68 (FIG. 2). The mixture serves to cool the area being treated by bur 42.

Referring again to FIG. 8, gasket 146 prevents any leakage of air or water from conduits 92 and 90, respectively.

Referring now to FIG. 6, it is seen that the light emanating from bulb 110 is projected against the end of the fiber optic bundle 84 (FIG. 4) in conduit 78. As pointed out above, the fiber optic bundle is bifurcated within handle 24, and is formed into bundles 58 (FIG. 3). The light emanates from termini 64, and illuminates the area being worked on.

Figure 9:
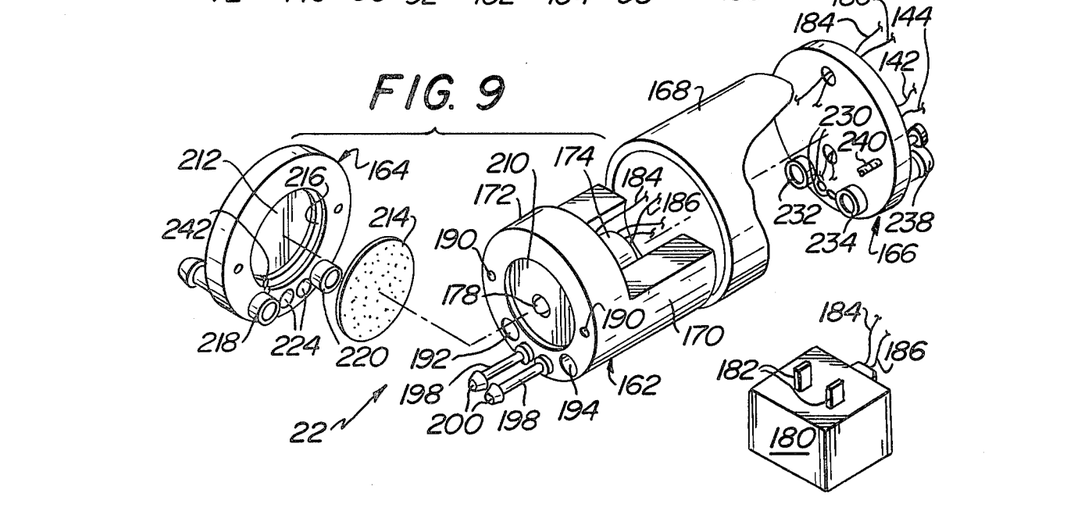
FIG. 9 is an exploded view of the pneumatic switch of this invention.
Figure 12:
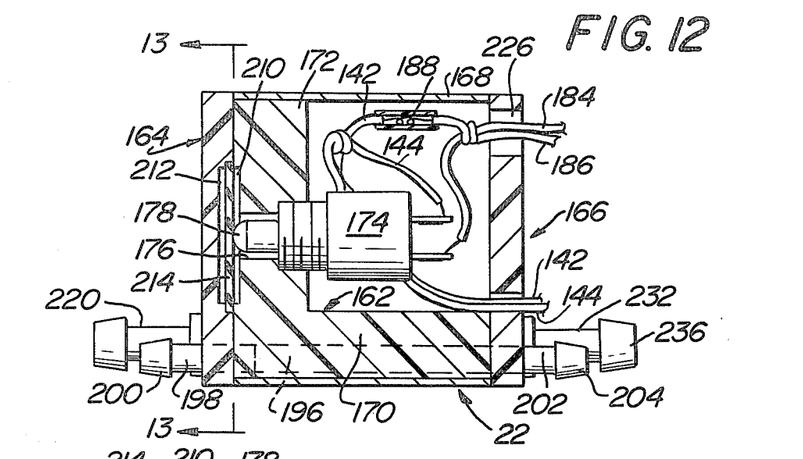
FIG. 12 is an enlarged sectional view taken along the line 12—12 of FIG. 10.

The control for the handpiece of this invention is shown in exploded perspective at 22 in FIG. 9. The control comprises a switch housing 162, an end plate 164, an end plate 166 and a cylindrical cover 168. Switch housing 162 includes a base 170 and an upstanding wall 172 at one end thereof. Threadedly secured in the wall 172 is a switch 174 (FIG. 12). Wall 172 has an opening 176 formed therein, and a depressible button 178 projects through said opening. Switch 174 is alternately opened and closed whenever button 178 is depressed.

Switch 174 is electrically connected to a transformer 180 (FIG. 9). Transformer 180 includes a pair of prongs 182, which are adapted to be inserted into a conventional wall receptable. Lines 184 and 186 are electrically connected to the transformer 180. Transformer 180 is a conventional transformer adapted to transform line voltage of 110 volts to 3.75 volts.

As seen in FIG. 12, line 184 is connected to switch 174, as by soldering. Line 186 is connected to line 142 by connector 188. Line 144 is connected to switch 174, and lines 142 and 144 pass through end plate 166 of control 22. As seen in FIG. 4, lines 142 and 144 pass from control 22 to the handpiece 20, where there are electrically connected to bulb 110 through leads 126 and 128, are used for controlling the actuation of the bulb.

Referring to FIG. 9, it is seen that base 170 of switch housing 162 includes a pair of upper channels 190 passing therethrough. A pair of lower channels 192 and 194 also pass through the base 170. Lowermost on base 170 are a pair of channels 196 (one shown in FIG. 12).

Conduits 198 having ferruled ends 200 are secured in one end of each of channels 196. Conduits 202 (one shown in FIG. 12) are secured in the other ends of channels 196, and these conduits have ferruled end 204.

As seen in FIG. 9, wall 172 of housing 162 includes a circular recess 210, into which pushbutton 178 projects. As seen in FIGS. 9 and 12, end wall 164 includes a circular recess 212, of the same size as recess 210. Recesses 210 and 212 are separated by a flexible rubber diaphragm 214, which is mounted against a shoulder 216 in end wall 164 (see FIG. 9). As seen in FIG. 12, the end of button 178 contacts diaphragm 214.

Figure 11:
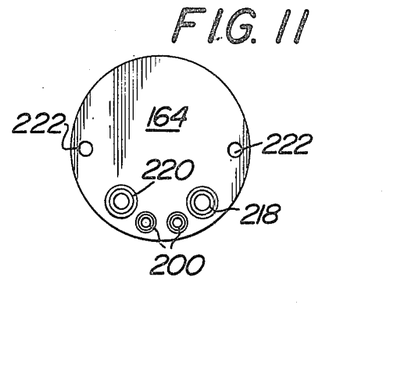
FIG. 11 is an elevational view of the other end of the switch of this invention.

As seen in FIGS. 9 and 11, a pair of ferruled conduits 218 and 220 pass through end wall 164. End wall 164 also includes a pair of tapped holes 222. A pair of holes 224 are formed in the bottom of wall 164 (FIG. 9), and when wall 164 is mounted against wall 172 of housing 162, the conduits 198, having ferruled ends 200, pass through wall 164 (FIG. 11).

Figure 10:
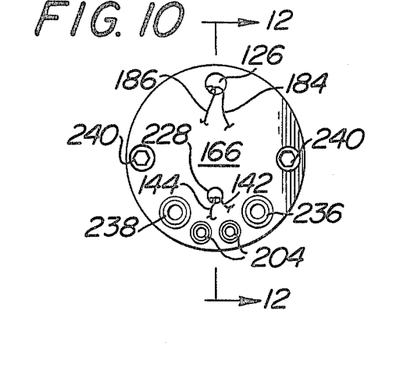
FIG. 10 is an elevational view of one end of the switch of this invention.

Referring to FIG. 10, it is seen that end wall 166 includes an upper opening 226, through which lines 184 and 186 pass. End wall 166 also includes a lower opening 228, through which lines 142 and 144 pass. End wall 166 includes lower openings 230 (FIG. 9) through which conduits 202 having a ferruled ends 204 pass. End wall 166 also includes a pair of conduits 232 and 234 (FIG. 9) having a ferruled ends 236 and 238, respectively.

The assembled condition of the control assembly 22 is shown in FIG. 12. In assembling the device, the end wall 164, with the diaphragm 214 in place, is placed into abutment with wall 172 of housing 162. Conduits 218 and 220 (FIG. 9) are inserted in channels 192 and 194, respectively. Thereafter, cylindrical cover 168 is slid over housing 162, and abuts end wall 164. When end wall 164 is set in place, conduits 198 pass through openings 224 in the end wall, with their ferrules 200 being shown in FIG. 11. Thereafter, end wall 166 is placed against housing 162. In doing so, conduits 232 and 234 enter channels 192 and 194, respectively. Additionally, conduits 202 project through openings 230, with their ferrules 204 being shown in FIG. 10. Lines 184, 186, 142 and 144 are passed through their respective openings in end wall 166. The entire assembly is held together by screws 240 (FIGS. 9 and 10), which pass through the end wall 166, through channels 190, and are threadedly received in tapped holes 222 in end wall 164 (FIG. 11).

Figure 13:
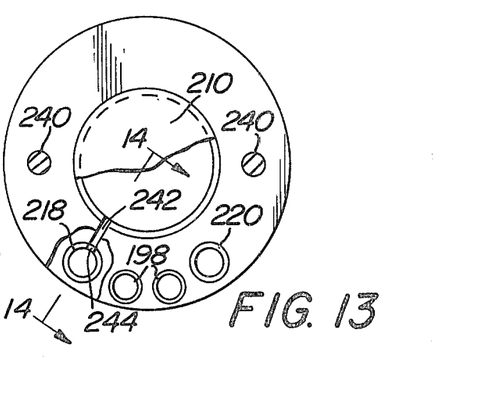
FIG. 13 is a sectional view taken along the line 13—13 of FIG. 12.
Figure 14:
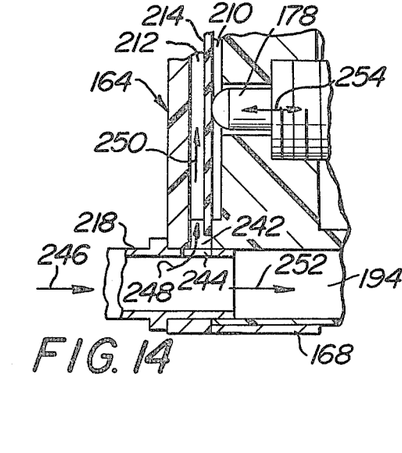
FIG. 14 is a sectional view taken along the line 14—14 of FIG. 13.

Referring to FIGS. 9, 13 and 14, it is seen that end wall 164 has a channel 242 formed therein. Channel 242 is in fluid communication with opening 244 in conduit 218 (FIG. 14).

The control mechanism is used by first inserting transformer 180 in a convenient receptacle. When the dentist that is using handpiece 20 depresses his foot pedal, air, under pressure, is admitted through conduit 218. Conduit 218 can be connected to a source of air under pressure by any conventional flexible tubing.

The air enters the conduit in the direction of arrow 246 (FIG. 14). A portion of the incoming air passes through opening 244 and channel 242, into the cavity formed by recess 212 and diaphragm 214 (FIG. 12), as indicated by arrows 248 and 250 in FIG. 14. When the air under pressure fills the cavity formed by recess 212 and diaphragm 214, the diaphragm expands against pushbutton 178 and into cavity 210. This depresses the pushbutton 178, and closes switch 174. When the switch is closed, current passes through the switch and through lines 142 and 144 to the handpiece 20, where it illuminates bulb 110.

At the same time switch 174 is closed, the bulk of the air entering conduit 218 passes through channel 194 in housing 162, as indicated by arrow 252 in FIG. 14. After passing through the channel, the air exits through conduit 234 in end wall 166. The exiting air enters handpiece 20 through flexible tube 136, which is connected to ferruled end of conduit 234 (see FIG. 7). The air is then used to drive the turbine 32.

The exhaust air emanating from the turbine housing is used to cool the bulb 110 and its associated sleeve 114, as described above. The exhaust air leaves handpiece 20 through flexible tubing 138, which has its other end connected on the ferruled end 236 of conduit 232. The exhaust air will pass through housing 162 and leave the control assembly through conduit 220, where it can be vented through flexible tubing to any convenient area.

When a dentist depresses his foot pedal to obtain the drive air for the handpiece, at the same time, the air and water supplies for the coolant spray, which exits from tube 68 (FIG. 3), are actuated. The air and water for the coolant spray are furnished through flexible tubing connected on conduits 198 (FIG. 9). The air and water then pass through channels 196 in housing 162, and exit through conduits 202 (FIG. 12). The air and water conduits are respectively connected with flexible tubes 134 and 132 (FIG. 8), from which they pass through the handpiece and exit from tube 68.

When the dentist removes the pressure from the foot pedal, the supply of drive air is automatically terminated, as is the supply of coolant air and water. This removes the pressure from diaphragm 214, and pushbutton 178 is spring-urged forwardly against diaphragm 214, thereby opening switch 174. The reciprocal movement of the pushbutton 178 is indicated by arrow 254 in FIG. 14. Switch 174 is a conventional pushbutton type switch, and the pressure of the air against diaphragm 214 will easily depress the pushbutton 178 to close the switch. Similarly, when the pressure against diaphragm 214 is removed, the pushbutton 178 will immediately be spring-urged forward, thereby opening the switch. It is thus seen that whenever the supply of air to the handpiece is ceased, switch 174 will immediately open, thereby removing the supply of current to bulb 110. This insures that the bulb will not be illuminated when there is no source of coolant air available.

The control assembly 22 can conveniently be mounted at any location within the dentist's office. A preferable location would be on the dentist's console or tray, in order to minimize the amount of tubing that the dentist must support when utilizing the handpiece. Since the bulb is contained within the handpiece, there is no necessity of having a long fiber optic line connecting a remote source of light with the dentist's handpiece.

One of the features of this invention is the control system 22. The control system can easily be serviced by merely removing screws 240 and end walls 164 and 166. If the diaphragm 214 needs replacement, this can simply be done by the dentist, merely by taking out the diaphragm and putting a new diaphragm in place. Additionally, if the switch 174 need be replaced, this can also be easily done, either by a dentist or a service technician.

As pointed out above, the pneumatic switch presently being used by the license of U.S. Pat. No. 4,334,863 includes a metal diaphragm wherein a circuit is completed through the diaphragm by the expansion of the diaphragm. The switch is in a sealed housing, and if the switch should malfunction, the entire switch has to be replaced. The serviceability of the switch of this invention provides a marked advantage over the switch presently in use.

The direct contact between the exhaust air and the bulb in the housing 86 provides for excellent cooling of the bulb and its associated sleeve 114. The heat-resistant plastic of the housing 86 reduces the amount of heat that will reach the dentist's hand when using the handpiece.

Although the invention has been described in connection with using fiber optic bundles for transmitting the light from the bulb 110, is should be understood that other light transmitting means can be used, such as quartz rods.

Although handle 24 and coupling 26 have been described as separate parts, in combination they comprise a hollow handle housing all of the internal parts of the handpiece, including the fiber optic lighting system.

Without further elaboration, the foregoing will so fully illustrate our invention, that others may, be applying current or future knowledge, readily adapt the same for use under various conditions of service.

We claim:

1. In a dental handpiece comprising a hollow handle and a rotatable chuck mounted at one end thereof, the improvement comprising a fiber optic lighting system within said handle, said fiber optic lighting system comprising a plurality of light transmitting fibers, a bulb housing within said handle, said bulb housing being formed of a heat-resistant plastic having a bulb-receiving channel therein, a bulb mounted within the channel of said housing with heat-resistant plastic of said housing interposed between the bulb and the handle, said fibers having one end terminating adjacent said bulb and the other end terminating at said end of said handle, whereby light emanating from said bulb passes through said fibers and to the area adjacent said end of said handle, and whereby said heat-resistant plastic reduces heat transfer from said bulb to said handle.

2. The dental handpiece of claim 1, and further including means for cooling said bulb.

3. The dental handpiece of claim 2 wherein said means for cooling said bulb comprises a source of air, with said air passing over and contacting said bulb.

4. The dental handpiece of claim 1 wherein said plastic comprises polytetrafluoroethylene.

5. A dental handpiece comprising a hollow handle, a turbine mounted at one end thereof, means for securing a dental bur within said turbine, means for supplying air to rotate said turbine, a fiber optic lighting system mounted within said handle, said system including a bulb housing formed from heat-resistant plastic having a bulb-receiving channel therein, a bulb mounted within the channel of said housing with heat-resistant plastic of said housing interposed between the bulb and the handle, light transmitting fibers within the channel of said housing, said fibers having one end terminating adjacent said bulb and the other end terminating at said end of said handle, whereby light emanating from said bulb passes through said fibers and onto the area adjacent said bur, an air-receiving channel passing through said housing, and means for directing air through said air-receiving channel, whereby said air aids in cooling said bulb.

6. The dental handpiece f claim 5 wherein the air for cooling said bulb comprises the air exhausted from said turbine after said turbine has been rotated.

7. The dental handpiece of claim 5 wherein said air-receiving channel is in fluid communication with said bulb-receiving channel, whereby the air passing through said air-receiving channel contacts said bulb to aid in cooling said bulb.

8. The dental handpiece of claim 5 wherein said housing includes additional channels, with one of said additional channels being adapted to pass water therethrough and another of said additional channels being adapted to pass air therethrough, with the air and water from said additional channels mixing to form a coolant spray for said dental bur.

9. The dental handpiece of claim 5 wherein said handle comprises a forward portion and a hollow coupling secured thereon, gasket means within said handle, said gasket means bearing against the rear of said forward portion, said housing bearing against said gasket means, and said coupling urging said housing against said gasket means.

10. The dental handpiece of claim 5 wherein said housing is separated from said handle by an annular recess, said recess serving to reduce the heat transfer from said housing to said handle.

11. The dental handpiece of claim 5 wherein said plastic comprises polytetrafluoroethylene.

12. The dental handpiece of claim 5, and further including control means for illuminating said bulb, said control means being actuated when said air is supplied to said handpiece.

13. The dental handpiece of claim 12 wherein said control means is pneumatically actuated by said supply air.

14. The dental handpiece of claim 13 wherein said control means comprises a pushbutton switch and a rubber diaphragm adjacent the pushbutton of said switch, said diaphragm being expanded into said pushbutton to depress the same when air is admitted to said control means, thereby closing said switch and illuminating said bulb, and said diaphragm releasing its pressure on said pushbutton when the supply of air is terminated, thereby opening said pushbutton switch.

15. The dental handpiece of claim 13 wherein said control means comprises a switch housing and end walls for said switch housing, said end walls being removable, said switch housing including a pushbutton switch and a diaphragm, said diaphragm resting in one of said end walls and being replaceable, said diaphragm serving to depress the pushbutton on said pushbutton switch when air under pressure is admitted against said diaphragm, thereby closing said switch, and said pushbutton switch opening when the source of air is terminated, with said pushbutton switch controlling the illumination of said bulb.

16. The dental handpiece of claim 15 wherein said diaphragm comprises rubber.

* * * * *